US010329361B2

(12) United States Patent
Kennedy et al.

(10) Patent No.: US 10,329,361 B2
(45) Date of Patent: Jun. 25, 2019

(54) QUANTITATIVE PREPARATION OF ALLYL TELECHELIC POLYISOBUTYLENE UNDER REFLUX CONDITIONS

(71) Applicants: Joseph P. Kennedy, Akron, OH (US); Tejal J. Deodhar, Akron, OH (US); Balazs L. Keszler, Fairlawn, OH (US)

(72) Inventors: Joseph P. Kennedy, Akron, OH (US); Tejal J. Deodhar, Akron, OH (US); Balazs L. Keszler, Fairlawn, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 39 days.

(21) Appl. No.: 15/795,638

(22) Filed: Oct. 27, 2017

(65) Prior Publication Data

US 2018/0127524 A1 May 10, 2018

Related U.S. Application Data

(60) Provisional application No. 62/414,038, filed on Oct. 28, 2016, provisional application No. 62/425,370, filed on Nov. 22, 2016.

(51) Int. Cl.
*C08F 110/10* (2006.01)
*C08F 2/01* (2006.01)
(Continued)

(52) U.S. Cl.
CPC .......... *C08F 110/10* (2013.01); *C07C 22/04* (2013.01); *C08F 2/01* (2013.01); *C08F 2/06* (2013.01);
(Continued)

(58) Field of Classification Search
CPC .. C08F 110/10; C08F 2/38; C08F 4/16; C08F 2/01; C08F 2/06; C08F 2500/01;
(Continued)

(56) References Cited

U.S. PATENT DOCUMENTS

| 4,758,631 A | 7/1988 | Kennedy et al. |
| 2006/0223946 A1* | 10/2006 | Faust ........................ C08F 8/00 525/314 |

OTHER PUBLICATIONS

B. Ivan, J.P. Kennedy J.; Polym. Sci., Part A: Polym Chem. 1989, 28, 89-104.

(Continued)

*Primary Examiner* — William K Cheung
(74) *Attorney, Agent, or Firm* — Renner Kenner Greive Bobak Taylor & Weber

(57) ABSTRACT

In one or more embodiments, the present invention provides a method for forming allyl telechelic polyisobutylene polymers having well defined molecular weights and molecular weight distributions using living cationic polymerization under ideal temperature control using a mixture of polar and nonpolar refluxing solvents. The methods according to various embodiments of the present invention provide temperature control that approaches the ideal, i.e., the heat of polymerization is instantaneously absorbed by the medium and the temperature of the system remains unchanged. The heat generated during the exothermic polymerization of isobutylene is released as an increase in the rate of reflux, rather than the temperature, since the temperature is set by the boiling point of the system and does not change.

20 Claims, 9 Drawing Sheets

(51) Int. Cl.
*C08F 2/06* (2006.01)
*C08F 2/38* (2006.01)
*C07C 22/04* (2006.01)

(52) U.S. Cl.
CPC ............ *C08F 2/38* (2013.01); *C08F 2400/02* (2013.01); *C08F 2500/04* (2013.01); *C08F 2810/30* (2013.01); *C08F 2810/40* (2013.01)

(58) Field of Classification Search
CPC .............. C08F 2500/02; C08F 2500/04; C08F 2810/40; C08F 2810/30; C08F 2400/02; C08C 22/04; C07C 22/04
USPC ......................................................... 526/89
See application file for complete search history.

(56) References Cited

OTHER PUBLICATIONS

G. Erdodi, J. Kang, J.P. Kennedy, E. Yilgor, I. Yilgor J.; Polym. Sci.: Part A; Polym. Chem., 2009, 47, 5278-5290.

\* cited by examiner

QUANTITATIVE PREPARATION OF ALLYL TELECHELIC POLYISOBUTYLENE UNDER REFLUX CONDITIONS

CROSS REFERENCE TO RELATED APPLICATIONS

This application claims the benefit of U.S. Provisional Patent Application Ser. No. 62/414,038 entitled "Isobutylene Polymerization in Refluxing Propane," filed Oct. 28, 2016 and U.S. Provisional Patent Application Ser. No. 62/425,370 entitled "Quantitative Preparation of Allyl Telechelic Polyisobutylene Under Reflux Conditions," filed Nov. 22, 2016, both of which are incorporated herein by reference in their entirety.

FIELD OF THE INVENTION

One or more embodiments of the present invention relates to formation of polyisobutylene by living cationic polymerization. In certain embodiments, the present invention relates to the quantitative formation of allyl telechelic polyisobutylene by living polymerization in refluxing solvents under ideal temperature control conditions. The invention further relates to a method for making polyisobutylene by the living cationic polymerization of isobutylene under reflux conditions. Advantageously, such a method allows for the production of polyisobutylene by living cationic polymerization at temperatures well above −78° C. without undesired side reactions during polymerization.

BACKGROUND OF THE INVENTION

Telechelic polyisobutylenes (PIBs) are of great commercial and scientific interest. Specifically, allyl-telechelic polyisobutylene (allyl-PIB-allyl), which can be made only by living polymerization, is the key ingredient for the preparation of biostable PIB-based polyurethanes, and various adhesives and sealants. Allyl-PIB-allyl is also an intermediate for the preparation of block copolymers, potting gels, surfactants, pressure sensitive adhesives, and non-stick chewing gum. Living IB polymerizations are most valuable for the preparation of predictable molecular weights and narrow dispersity products. The significance of this methodology, however, goes far beyond molecular weight (MW) and molecular weight distribution (MWD) control, and, in addition to making allyl-PIB-allyl, it can be used for the preparation of a great variety of telechelics, block polymers, etc.

The synthesis of allyl-PIB-allyl at cryogenic temperatures has been described. See, B. Ivan, J. P. Kennedy, *J. Polym. Sci., Part A: Polym Chem.* 1989, 28, 89-104 and J. P. Kennedy, B. Ivan, In Designed Polymers by Carbocationic Macromolecular Engineering; Hanser Verlag, Munich, 1992, the disclosures of which are incorporated herein by reference. Traditionally, the cooling of isobutylene (IB) polymerization charges to low temperatures is necessary to "freeze out" undesirable side reactions during polymerization, the most deleterious of which is chain transfer to monomer. This side reaction produces two polymer molecules with unsaturated end groups, i.e., an exo and an endo unsaturation, by proton loss of the propagating tertiary cation, plus a new tert butyl cation that sustains further propagation (See, Scheme 1, below).

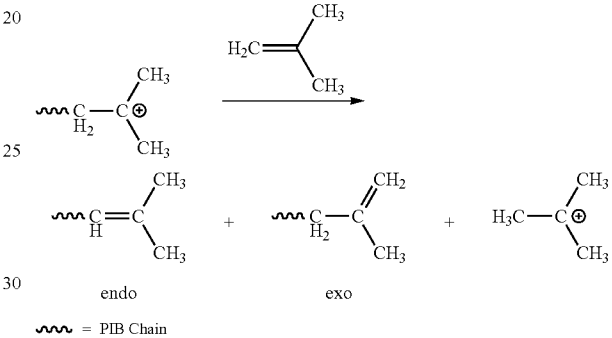

Scheme 1
Undesirable chain transfer to monomer reaction

The predominant product of chain transfer is the polymer carrying the exo double bond while that with endo unsaturation is a minor component. Mechanistic details of chain transfer are beyond the scope of this application and have been described elsewhere. See generally, G. Erdodi, J. Kang, J. P Kennedy, E. Yilgor, I. Yilgor, *J. Polym. Sci.: Part A: Polym. Chem.*, 2009, 47, 5278-5290 and Published U.S. Patent Application No. 1988/4758631 to Kennedy et al., the disclosures of which are incorporated herein by reference.

Another undesirable side reaction that can occur in these reactions involves the active propagating cation plus the exo double bond at the terminus of a polymer formed by deprotonation (see, Scheme 1, above). This alkylation followed by proton loss (sometimes called "coupling"), yields ill-defined high molecular weight byproducts (See, Scheme 2, below).

Scheme 2

Undesirable coupling reaction

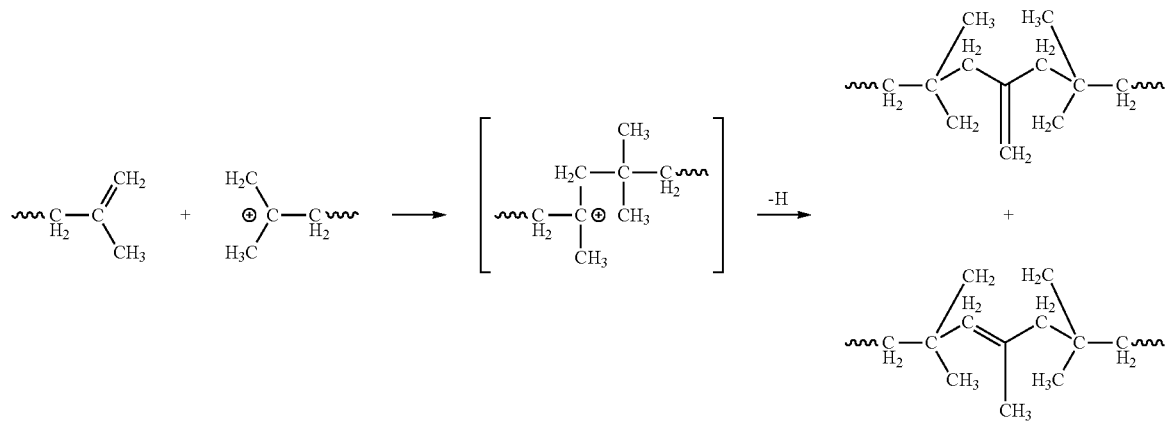

∿∿ = PIB Chain

It is known that these undesirable reactions may occur if the polymerization is carried out at a relatively high temperature or is not quenched (terminated) as soon as practicable after complete monomer conversion and the system remains active in the absence of monomer.

The rate of IB polymerization in these living cationic polymerization reactions is very high, virtually instantaneous upon coinitiator addition, and monomer conversions reach near completion within seconds. Thus, it has been very difficult to obtain rate constants needed for designing process conditions. Further, the polymerization is known to be highly exothermic, making it is very difficult to maintain a constant reaction temperature. And if the heat of reaction is not completely removed and the temperature increases, byproduct formation by side reactions increases. In practice, the high heat of reaction is mitigated by the use of costly high efficiency stirrers and special cooling equipment.

It has been known for some time that refluxing solvents may be used to mitigate heat evolution of exothermic reactions. Under reflux conditions the heat of polymerization is instantaneously absorbed by the refluxing medium and the temperature remains unchanged. The heat generated during exothermic polymerization merely increases the rate of reflux and the temperature does not change because it is set by the boiling point of the system. The increased rate of reflux is also beneficial as it contributes to the mixing of the charge and obviates the use of high cost stirring and cooling equipment. On reaction completion, the refluxing solvent(s) can be easily removed by evaporation at room temperature, recovered and reused. Thus, product recovery is facilitated and cumbersome workup is avoided or simplified.

What is needed in the art is a method for the synthesis of allyl-PIB-allyl with quantitative allylation of living ends using living cationic polymerization under ideal temperature control, or at least increased temperatures, using refluxing solvents.

SUMMARY OF THE INVENTION

In one or more embodiments, the present invention provides a method for forming telechelic polyisobutylene polymers having well defined molecular weights and molecular weight distributions using living cationic polymerization under ideal temperature control using a mixture of polar and nonpolar refluxing solvents. The methods of forming telechelic polyisobutylene polymers according to various embodiments of the present invention provide temperature control that approaches the ideal, i.e., the heat of polymerization is instantaneously absorbed by the medium and the temperature of the system remains unchanged. The heat generated during exothermic polymerization is released as an increase in the rate of reflux, rather than the temperature, since the temperature is set by the boiling point of the system and cannot change. Moreover, these methods obviate the use of expensive and cumbersome external cooling equipment and the increased rate of refluxing contributes to efficient mixing of the charge. Also, product recovery is greatly facilitated because the refluxing solvent(s) can be removed by simply removing the reflux condenser and letting the solvents evaporate at room temperature. In this manner cumbersome filtration, precipitation, etc. are obviated and product recovery is greatly simplified.

In a first aspect, the present invention is directed to a method for making polyisobutylene by living cationic polymerization of isobutylene comprising: (A) providing an externally cooled reaction vessel; (B) charging the externally cooled reaction vessel with isobutylene, an initiator, a refluxing solvent mixture, and a proton trap and/or electron donor, at a temperature below a boiling point for the refluxing solvent mixture; (C) allowing the temperature of the externally cooled reaction vessel to increase to the boiling point of the refluxing solvent mixture causing the refluxing solvent mixture to reflux; (D) inducing living cationic polymerization of the isobutylene by the addition of a co-initiator to the externally cooled reaction vessel to produce polyisobutylene polymer chains; and (E) terminating the living cationic polymerization reaction to produce the polyisobutylene polymer. In some embodiments, the externally cooled reaction vessel is equipped with a reflux condenser.

In one or more embodiments, the method for making polyisobutylene by living cationic polymerization of isobutylene of the present invention includes any one or more of the above referenced embodiments of the first aspect of the present invention wherein the refluxing solvent mixture comprises a polar solvent and a nonpolar solvent. In some embodiments, the nonpolar solvent is propane. In some of these embodiments, the polar solvent is methyl chloride ($CH_3Cl$) r dichloromethane ($CH_2Cl_2$).

In one or more embodiments, the method for making polyisobutylene by living cationic polymerization of isobutylene of the present invention includes any one or more of the above referenced embodiments of the first aspect of the present invention wherein the volume ratio of propane to methyl chloride in the refluxing solvent mixture is from about 9:1 to about 1:9. In one or more embodiments, the method for making polyisobutylene by living cationic polymerization of isobutylene of the present invention includes any one or more of the above referenced embodiments of the first aspect of the present invention wherein the volume ratio of propane to methyl chloride in the refluxing solvent mixture is from about 7.5:2.5 to about 3:2. In one or more embodiments, the method for making polyisobutylene by living cationic polymerization of isobutylene of the present invention includes any one or more of the above referenced embodiments of the first aspect of the present invention wherein the ratio of propane to methyl chloride in the refluxing solvent mixture by volume is from about 3:2 to about 7:3. In one or more embodiments, the method for making polyisobutylene by living cationic polymerization of isobutylene of the present invention includes any one or more of the above referenced embodiments of the first aspect of the present invention wherein the ratio of propane to methyl chloride in the refluxing solvent mixture by volume is about 6.5:3.5.

In one or more embodiments, the method for making polyisobutylene by living cationic polymerization of isobutylene of the present invention includes any one or more of the above referenced embodiments of the first aspect of the present invention wherein the refluxing solvent mixture has a boiling point of about −40° C.

In one or more embodiments, the method for making polyisobutylene by living cationic polymerization of isobutylene of the present invention includes any one or more of the above referenced embodiments of the first aspect of the present invention wherein the initiator is 1-(tert-butyl)-3,5-bis(2-chloropropan-2-yl)benzene (HDCCl). In one or more embodiments, the method for making polyisobutylene by living cationic polymerization of isobutylene of the present invention includes any one or more of the above referenced embodiments of the first aspect of the present invention wherein the proton trap is tetramethylethylene-diamine (TMEDA). In one or more embodiments, the method for making polyisobutylene by living cationic polymerization of isobutylene of the present invention includes any one or more of the above referenced embodiments of the first aspect of the present invention wherein co-initiator is titanium tetrachloride ($TiCl_4$).

In one or more embodiments, the method for making polyisobutylene by living cationic polymerization of isobutylene of the present invention includes any one or more of the above referenced embodiments of the first aspect of the present invention wherein the living cationic polymerization reaction is allowed to continue for about 15 minutes or until substantially all of the isobutylene has been reacted before the step of termination. In one or more embodiments, the method for making polyisobutylene by living cationic polymerization of isobutylene of the present invention includes any one or more of the above referenced embodiments of the first aspect of the present invention wherein the step of terminating the polymerization reaction comprises adding a termination agent, wherein the termination agent terminates the living cationic polymerization reaction by reacting with the polyisobutylene chains to leave terminal allyl functional groups on the polyisobutylene chains. In one or more embodiments, the method for making polyisobutylene by living cationic polymerization of isobutylene of the present invention includes any one or more of the above referenced embodiments of the first aspect of the present invention wherein the polyisobutylene polymer produced in has a molecular weight distribution of from 1.0 to 1.2 and a number average end functionalization ($f_n$) of from about 1.8 to about 2.0.

In a second aspect, the present invention is directed to a method for controlling the reaction temperature of living cationic polymerization of isobutylene conducted above −78° C. comprising: (A) providing an externally cooled reaction vessel; (B) charging the externally cooled reaction vessel with isobutylene, an initiator, a refluxing solvent mixture, and a proton trap at a temperature below a boiling point for the refluxing solvent mixture, wherein the refluxing solvent mixture comprises a polar solvent and a nonpolar solvent; (C) allowing the temperature of the externally cooled reaction vessel to increase to the boiling point of the refluxing solvent mixture causing the refluxing solvent mixture to reflux; (D) inducing living cationic polymerization of the isobutylene by the addition of a co-initiator to the externally cooled reaction vessel to produce polyisobutylene polymer chains; wherein the temperature inside the externally cooled reaction vessel is maintained at or about the boiling point during the living cationic polymerization. In some of these embodiments, the refluxing solvent mixture has a boiling point of about −40° C.

In one or more embodiments, the method for controlling the reaction temperature of living cationic polymerization of isobutylene of the present invention includes any one or more of the above referenced embodiments of the second aspect of the present invention wherein the nonpolar solvent is propane and the polar solvent is methyl chloride. In one or more embodiments, the method for controlling the reaction temperature of living cationic polymerization of isobutylene of the present invention includes any one or more of the above referenced embodiments of the second aspect of the present invention wherein the refluxing solvent mixture comprises from about 60% to about 70% propane and from about 30% to about 40% methyl chloride by volume. In one or more embodiments, the method for controlling the reaction temperature of living cationic polymerization of isobutylene of the present invention includes any one or more of the above referenced embodiments of the second aspect of the present invention wherein the refluxing solvent mixture comprises 65% propane and 35% methyl chloride by volume.

In a third aspect, the present invention is directed to a method of making a di-telechelic allyl-functionalized polyisobutylene by living cationic polymerization of isobutylene comprising: (A) providing an externally cooled reaction vessel equipped with a reflux condenser; (B) charging the externally cooled reaction vessel with isobutylene, a bi-functional PIB initiator, a refluxing solvent mixture comprising propane and methyl chloride, and a proton trap and/or electron donor at a temperature below a boiling point for the refluxing solvent mixture; (C) allowing the temperature of the externally cooled reaction vessel to increase to the boiling point of the refluxing solvent mixture causing the refluxing solvent mixture to reflux; (D) inducing living cationic polymerization of the isobutylene by the addition of a co-initiator to the externally cooled reaction vessel to produce polyisobutylene polymer chains; (E) allowing living cationic polymerization to continue until substantially all of the isobutylene has been reacted; (F) terminating the living cationic polymerization reaction by adding a termination agent, wherein the termination agent terminates the living cationic polymerization reaction by reacting with the polyisobutylene chains to leave terminal allyl functional groups on the polyisobutylene chains to produce the di-telechelic allyl-functionalized polyisobutylene. In some of these embodiments, the refluxing solvent mixture has a boiling point of about −40° C.

In one or more embodiments, the method making a di-telechelic allyl-functionalized polyisobutylene by living cationic polymerization of isobutylene of the present invention includes any one or more of the above referenced embodiments of the third aspect of the present invention wherein the bi-functional initiator comprises 1-(tert-butyl)-3,5-bis(2-chloropropan-2-yl)benzene (HDCCl).

In one or more embodiments, the method making a di-telechelic allyl-functionalized polyisobutylene by living cationic polymerization of isobutylene of the present invention includes any one or more of the above referenced embodiments of the third aspect of the present invention wherein the step of terminating is performed about 15 minutes after the step inducing. In one or more embodiments, the method making a di-telechelic allyl-functionalized polyisobutylene by living cationic polymerization of isobutylene of the present invention includes any one or more of the above referenced embodiments of the third aspect of the present invention wherein the step of terminating is performed not more than 5 minutes after all of the isobutylene has reacted.

In one or more embodiments, the method making a di-telechelic allyl-functionalized polyisobutylene by living cationic polymerization of isobutylene of the present invention includes any one or more of the above referenced embodiments of the third aspect of the present invention wherein the refluxing solvent mixture comprises from about 60% to about 70% propane and from about 30% to about 40% methyl chloride by volume. In one or more embodiments, the method making a di-telechelic allyl-functionalized polyisobutylene by living cationic polymerization of isobutylene of the present invention includes any one or more of the above referenced embodiments of the third aspect of the present invention wherein the refluxing solvent mixture comprises 65% propane and 35% methyl chloride by volume.

In one or more embodiments, the method making a di-telechelic allyl-functionalized polyisobutylene by living cationic polymerization of isobutylene of the present invention includes any one or more of the above referenced embodiments of the third aspect of the present invention wherein the di-telechelic allyl-functionalized polyisobutylene produced has a molecular weight distribution of from about 1.0 to about 1.2 and a number average end functionalization ($f_n$) of from about 1.8 to about 2.0.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

Figure 1:
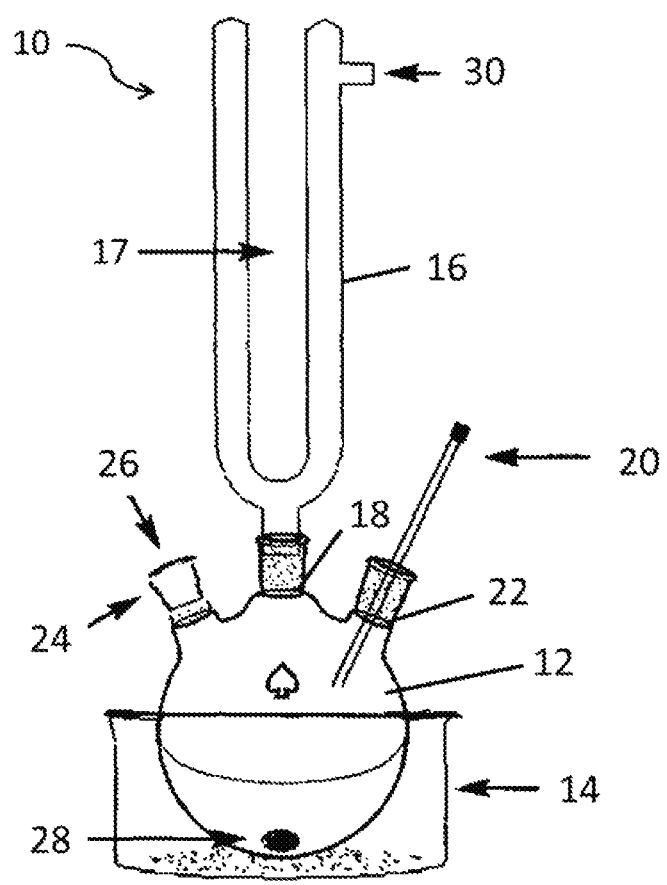
FIG. 1 is a schematic diagram showing equipment used for condensing propane and MeCl solvents and carrying out the synthesis of allyl-PIB-allyl according to one or more embodiments of the present invention.

In one or more embodiments, the present invention provides a method for forming telechelic polyisobutylene polymers having well defined molecular weights and molecular weight distributions using living cationic polymerization under ideal temperature control using a mixture of polar and nonpolar refluxing solvents. The methods of forming telechelic polyisobutylene polymers according to various embodiments of the present invention do not require the cryogenic temperatures (typically, Dry Ice temperature of −78° C.) and provide temperature control that approaches the ideal in that the heat of polymerization is instantaneously absorbed by the medium and the temperature of the system remains unchanged. The heat generated during the exothermic polymerization of isobutylene is released as an increase in the rate of reflux, rather than an increase in the temperature, since the temperature is set by the boiling point of the system and cannot change.

As set forth above, the methods of forming telechelic polyisobutylene polymers according to various embodiments of the present invention provide at least the following advantages: (a) temperature control approaches the ideal, i.e., the heat of polymerization is instantaneously absorbed by the medium and the temperature of the system remains unchanged because the heat generated during exothermic polymerization merely increases the rate of reflux but the temperature cannot change as it is set by the boiling point of the system; (b) the increased rate of refluxing is beneficial as it contributes to efficient mixing of the charge; (c) the refluxing charges ("internal cooling") obviate the use of expensive and cumbersome external cooling equipment; and (d) product recovery is greatly facilitated since the refluxing solvent(s) can be removed by simply removing the reflux condenser and letting the solvents evaporate at room temperature, thereby obviating the cumbersome filtration, precipitation, etc. and greatly simplifying product recovery.

In one or more embodiments, the living cationic polymerization reactions of the present invention will take place in a suitable reaction apparatus. The reaction apparatus will include a reaction vessel, as is known in the art. Any suitable vessel of a desired volume that is capable of tolerating the temperatures and pressures generated by the living cationic polymerizations described herein may be used. In some of these embodiments, the reaction vessel may be a three necked round bottom flask rated for use at temperatures at or below the boiling point of the refluxing solvent mixtures being used. One of ordinary skill in the art will be able to select a reaction vessel without undue experimentation.

The reaction apparatus will also include an external cooling mechanism that is capable of cooling the reaction vessel to temperatures at or below the boiling point of the refluxing solvent mixtures being used, which in the case of propane is about −42° C., depending upon the ambient pressure. The external cooling mechanism is not particularly limited and any suitable mechanism or apparatus known in the art may be used. In some embodiments, the external cooling mechanism comprises a removable cooling bath containing a mixture of dry ice and a suitable alcohol, such as isopropanol. These types of external cooling mechanisms are well known in the art and one of ordinary skill in the art would be able to configure a suitable external cooling mechanism without undue experimentation.

In various embodiments, the reaction apparatus will further include a reflux condenser operably connected to or integral with the reaction vessel. Any type of reflux condenser known in the art may be used, provided that it is capable of condensing the reflux solvents. As will be apparent, the reflux condenser must be able to get cold enough to bring the temperature of the gaseous reflux solvent or solvent mixture used back down below its boiling point for it to condense. These types of reflux condensers are well known in the art and one of ordinary skill in the art would be able to select a suitable reflux condenser without undue experimentation. In one or more embodiments, the reflux condenser may be a cold finger or Dewar type reflux condenser. In some embodiments, reflux condenser may be a Dewar type reflux condenser loaded with a mixture of dry ice and an alcohol having a low freezing point (below that of dry ice ($CO_2$)), such as isopropanol or acetone. In some embodiments, the reflux condenser will also include an inlet for receiving and flushing the reaction vessel with an inert gas, such as nitrogen gas. In addition, the reaction apparatus may, in various embodiments, include a thermocouple for measuring the reaction temperature inside of the reaction vessel, a rubber septa through which the reaction vessel may be charged and the coinitiator and termination agent added, and a magnetic stirrer.

In one or more embodiment, a reaction apparatus such as the one shown in FIG. 1 may be used. In one or more of these embodiments, the reaction apparatus 10 comprises a three neck round bottom flask 12, a removable external cooling bath 14 containing dry ice and isopropanol, a reflux condenser 16 containing dry ice and isopropanol 17 and mounted to the round bottom flask 12 at opening 18, a thermocouple 20 mounted to the round bottom flask 12 at opening 22, a rubber septa 24 mounted to the round bottom flask 12 at opening 26, a magnetic stirrer 28, and gas inlet port 30, arranged as shown in FIG. 1.

Next, the reaction vessel is cooled by the external cooling mechanism to a temperature that is at or below a boiling point for the refluxing solvent mixture using the external cooling mechanism described above and charged with isobutylene, an initiator, a refluxing solvent mixture, and a proton trap and/or electron donor. To facilitate the charging of the reaction vessel, it is preferred to cool the reaction vessel to a temperature that is below the boiling point of the refluxing solvent mixture does not begin to reflux immediately upon entering the reaction vessel.

The initiator used is not particularly limited and any initiator known in the art for initiating living cationic polymerization of isobutylene may be used. In one or more embodiments, suitable initiators may include, without limitation, those initiators disclosed in U.S. Pat. No. 5,733,998 to Kennedy et al., U.S. Pat. No. 8,889,926 to Kennedy et al., and/or Published International Application No. WO 2017/127642, the disclosures of which are incorporated herein by reference in their entirety. In some embodiments, the initiator is preferably bi-functional, and will initiate living cationic polymerization of isobutylene in two directions. However, the invention is not so limited and the initiator may also be monofunctional or multi-functional. For embodiments where the product is to be a di-telechelic allyl-functionalized polyisobutylene (allyl-PIB-allyl), the initiator may be any bi-functional initiator known in the art to initiate living cationic polymerization of isobutylene in two directions. In some of these embodiments, the initiator comprises 1-(tert-butyl)-3,5-bis(2-chloropropan-2-yl)benzene (HDCCl).

As set forth above, the method of the present invention further includes a refluxing solvent mixture comprising a polar and a non-polar solvent. As will be apparent, in various embodiments of the present invention the boiling point of the refluxing solvent mixture will be the temperature at which the living cationic polymerization reaction will take place. As used herein, the boiling point of the refluxing solvent mixture is the temperature at which the refluxing solvent mixture or any component thereof begins to boil and reflux. As will be apparent, the boiling point of the refluxing solvent mixture is dependent upon ratio of polar and non-polar solvents contained therein. See, FIG. 2. In various embodiments, the refluxing solvent mixture will have a boiling point that is at or below −10° C., to limit or "freeze out" any potential side undesirable reactions, such as those discussed above. And while not required, the boiling point of the refluxing solvent mixture is preferably higher than the cryogenic temperatures that are currently in use and are described above, so that the benefits of avoiding the difficulty and expense of known systems used to generate those temperatures may be avoided by the present invention. In some embodiments, the refluxing solvent mixture will have a boiling point of from about −78° C. to about −10° C., in other embodiments, from about −78° C. to about −20° C., in other embodiments, from about −78° C. to about −30° C., in other embodiments, from about −70° C. to about −40° C., in other embodiments, from about −60° C. to about −40° C., and in other embodiments, from about −78° C. to about −24° C. In one or more embodiments, the refluxing solvent mixture will have a boiling point of about −40° C.

As set forth above, in various embodiments, the refluxing solvent mixture comprises both a polar and a non-polar solvent. While the use of either a polar solvent or a non-polar solvent alone as the refluxing solvent will provide the benefit of temperature control as described herein, it has been found that these methods result in the formation polymers that are not well defined. (See, FIGS. 3 and 4) In various embodiments, any polar solvent or nonpolar solvent that is a solvent for isobutylene and/or one or more of the other reaction components, does not interfere in any way with the living cationic polymerization of isobutylene (as described herein), and has a boiling point as described above may be used. In one or more embodiment, the nonpolar solvent may be propane ($C_3H_8$), isobutene, or neopentane, and is preferably propane. In one or more embodiment, the polar solvent may be chloromethane (methyl chloride) ($CH_3Cl$), dichloromethane ($CH_2Cl_2$), chloroethane, or chlorobutane, and is preferably chloromethane.

In one or more embodiments, the ratio of polar solvent to nonpolar solvent (volume to volume) in the refluxing solvent mixture may be from about 1:9 to about 9:1, in other embodiments, from about 4:1 to about 1:4, in other embodiments, from about 2:3 to about 7.5:2.5, in other embodiments, from about 2:3 to about 7:3, in other embodiments, from about 3.5:6.5 to about 6.5:3.5, in other embodiments, from about 2:3 to about 3:2, in other embodiments, from about 4.5:5.5 to about 5.5:4.5, in other embodiments, from about 1:1 to about 7:3, in other embodiments, from about 2:3 to about 7:3, and in other embodiments, from about 3:2 to about 7:3. In some of these embodiments, the ratio of polar solvent to nonpolar solvent (volume to volume) in the refluxing solvent mixture may be 6.5:3.5. In some other of these embodiments, the ratio of polar solvent to nonpolar solvent (volume to volume) in the refluxing solvent mixture may be 3:2.

In one or more embodiments, the refluxing solvent mixture comprises propane (nonpolar solvent) and chloromethane (polar solvent) at volume percentages of from about 90/10 to about 10/90, in other embodiments, from about 80/20 to about 20/80, in other embodiments, from about 75/25 to about 40/60, in other embodiments, from about 70/30 to about 40/60, in other embodiments, from about 65/35 to about 35/65, in other embodiments, from about 60/40 to about 40/60, in other embodiments, from about 55/45 to about 45/55, in other embodiments, from about 50/50 to about 70/30, in other embodiments, from about 40/60 to about 70/30, and in other embodiments, from about 60/40 to about 70/30 of propane and chloromethane, respectively. In some of these embodiments, the refluxing solvent mixture comprises 65% propane and 35% chloromethane by volume. In some of these embodiments, the refluxing solvent mixture comprises 60% propane and 40% chloromethane by volume.

As set forth above, the reaction vessel is also charged with a proton trap or electron donor to promote living polymerization. The choice of proton trap or electron donor is not particularly limited and any proton trap or electron donor known in the art for use in living cationic polymerization of isobutylene may be used. In one or more embodiment, 2,5-di tert. butyl pyridine, tetramethylethylene-diamine (TMEDA), or a combination thereof may be used.

Once the reaction vessel has been charged, the temperature of the reaction vessel is allowed to increase to the boiling point of the refluxing solvent mixture causing the refluxing solvent mixture to reflux. The best method for doing this will, of course, depend upon the type of external cooling mechanism used and is well within the ability of one of ordinary skill in the art. In various embodiments, the external cooling mechanism may be turned down/shut off or the reaction vessel may be removed from the external cooling mechanism. In some embodiments, the external cooling mechanism is a dry ice or other cooling bath and the reaction vessel is simply removed from the cooling bath. In any event, when the increasing temperature of the reaction vessel reaches the boiling point of the refluxing solvent mixture, the system will begin to reflux as the refluxing solvent mixture boils and is condensed. As set forth above, once the reflux process begins, it effectively prevents the temperature in the reaction vessel from increasing and any additional heat that enters (or is generated within) the reaction vessel is dissipated by increases in the rate of reflux. In this manner, the method of various embodiments of the present invention achieves ideal temperature control over the reaction, in the sense that the reaction temperature will remain essentially the same throughout the process. (See FIGS. 5A-B).

Next, a coinitiator is added to the reaction vessel to induce living cationic polymerization of the isobutylene around the initiator in the charge to produce polyisobutylene polymer chains. The detailed reaction mechanisms for living cationic polymerization of isobutylene are well known in the art and need not be described in detail here. See, e.g., "Carbocationic Polymerizatrion" J. P. Kennedy and E. Marechal, Wiley 1982, and "Designed Polymers by Carbocartionic Macromolecular Engineering" J. P. Kennedy and B. Ivan, Wiley 1992, the disclosures of which are incorporated herein by reference in their entirety. Any coinitiator known in the art for inducing living cationic polymerization of the isobutylene may be used and one of ordinary skill in the art will be able to select a suitable coinitiator without undue experimentation. In various embodiments, suitable coinitiators may include, without limitation, titanium tetrachloride ($TiCl_4$), boron trichloride, stannic tetrachloride and/or other similar Friedel-Crafts acids. In one or more embodiments, the coinitiator is titanium tetrachloride ($TiCl_4$).

In various embodiments, the living cationic polymerization reaction is allowed to proceed until all or substantially all of the IB monomer has reacted, before being terminated. In some embodiments, all or substantially all of the IB monomer will react within about 10 minutes. See FIG. 6A. In one or more embodiments, the reaction is allowed to proceed for from about 10 minutes to about 20 minutes, in other embodiment, from 12 minutes to 18 minutes, in other embodiments, from about 14 minutes to about 16 minutes. In one or more embodiments, the living cationic polymerization reaction is allowed to proceed for about 15 minutes after the coinitiator is added, before being terminated as described below.

As set forth above, the rate of IB polymerization in these living cationic polymerization reactions is very high, virtually instantaneous upon coinitiator addition, and monomer conversions reach near completion within seconds. Not surprisingly, these reactions are also highly exothermic and generate a large amount of heat. As set forth above, however, the refluxing solvent systems of the present invention provide temperature control that approaches the ideal in that the heat of polymerization is instantaneously absorbed by the medium and the temperature of the system remains unchanged. The heat generated during the exothermic polymerization of isobutylene is released as an increase in the rate of reflux, rather than an increase in the temperature, since the temperature is set by the boiling point of the system and cannot change.

Finally, the living cationic polymerization reaction is terminated to produce a polyisobutylene polymer having terminal end groups. In various embodiments, the living cationic polymerization reaction is terminated by the addition of a termination agent that terminates polymerization, and preferably functionalizes the ends of the polyisobutylene chains. While other alternative termination methods are possible and contemplated by the present invention, in various embodiments of the present invention, it is preferred that the termination agent terminate polymerization by the addition of terminal allyl functional groups. In one or more of these embodiments, the termination agent will contain an allyl group and will react with the active propagating cations at the ends of the PIB chains thereby terminating the living cationic PIB polymerization reactions and leaving allyl functional groups at the ends of the PIB chains. (See, Scheme 3, below) Any termination agent known in the art for terminating living cationic polymerization of the isobutylene may be used and one of ordinary skill in the art will be able to select a suitable terminating agent without undue experimentation. In various embodiments, the termination agent may be allyl trimethyl silane (ATMS).

As set forth above, these living cationic polymerization reactions do not terminate of their own accord and remain "living" even after all of the IB monomer has reacted. The meaning of the term "living" as applied to living cationic polymerization of IB is as set forth in "Designed Polymers by Carbocartionic Macromolecular Engineering" J. P. Kennedy and B. Ivan, Wiley 1992, the disclosure of which is incorporated herein by reference in its entirety. To avoid undesired side reactions, however, these reactions are preferably terminated as soon as practicable following depletion of the IB monomer. It has been found that in one or embodiment of the present invention, these polymerization reactions can safely be allowed to stand for up to 5 minutes after depletion of the IB monomer before they should be terminated to avoid the occurrence of side reactions that may compromise product quality. In one or more embodiment, a well-defined allyl telechelic PIB can be obtained by terminating polymerization at least 15 minutes after coinitiator addition (i.e., in the absence of monomer).

In various embodiments, termination of the living cationic polymerization reactions by use of a terminating agent such as allyl trimethyl silane (ATMS), provides a well-defined allyl telechelic PIB having a molecular weight distribution of from 1.0 to 1.3 and a number average end functionalization ($f_n$) of from about 1.7 to about 2.0. In one or more of these embodiments, the allyl telechelic PIB will have a molecular weight distribution of from 1.0 to 1.2, and in other embodiments, from about 1.0 to 1.1. In one or more of these embodiments, the allyl telechelic PIB will have a number average end functionalization ($f_n$) of from 1.8 to 2.0, and in other embodiments, from about 1.9 to 2.0.

In one or more embodiments, the present invention is directed to a method of making a di-telechelic allyl-functionalized polyisobutylene by living cationic polymerization of isobutylene comprising: providing an externally cooled reaction vessel operably equipped with a reflux condenser; charging the externally cooled reaction vessel with isobutylene, a bi-functional initiator, such as HDCCl, a refluxing solvent mixture comprising from about 60% to about 70% propane and from about 30% to about 40% chloromethane, and a proton trap as described above, at a temperature below the boiling point for the refluxing solvent mixture; allowing the temperature of the reaction vessel to increase to the boiling point of the refluxing solvent mixture causing it to reflux; inducing living cationic polymerization of the isobutylene by the addition of a co-initiator as described above, preferably titanium tetrachloride (TiCl$_4$), to the externally cooled reaction vessel to produce polyisobutylene polymer chains; allowing living cationic polymerization to continue until substantially all of the isobutylene has been reacted; and then terminating the living cationic polymerization reaction by adding a termination agent as described above, such as allyl trimethyl silane (ATMS). In these embodiments, the termination agent terminates the living cationic polymerization reaction by reacting with the polyisobutylene chains to leave terminal allyl functional groups on the polyisobutylene chains to produce the di-telechelic allyl-functionalized polyisobutylene, as described above.

In still another aspect, the present invention is directed to a method for controlling the temperature for conducting living cationic polymerization of isobutylene at temperatures well above −78° C., but below about −10° C. In these embodiments, the method begins with providing an externally cooled reaction vessel and charging it with isobutylene, an initiator, a refluxing solvent mixture having a boiling point above −78° C., and a proton trap, as described above. In one or more of these embodiments, the refluxing solvent mixture will comprise propane (nonpolar solvent) and chloromethane (polar solvent) in a volume ratio of propane to chloromethane of from 6:4 to about 7:3). In these embodiments, the reaction vessel is charged at a temperature below the boiling point for the refluxing solvent mixture and the temperature of the reaction vessel is then allowed to increase to the boiling point of the refluxing solvent mixture, which begins to reflux. Finally, living cationic polymerization of the isobutylene is initiated by the addition of a co-initiator to the reaction vessel to produce polyisobutylene polymer chains while the reaction temperature is maintained at a controlled temperature equal to the boiling point of the refluxing solvent mixture (which is higher than −78° C.) by the action of the refluxing solvent mixture, as described above.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

Abbreviations

In this Example, the following abbreviations are used: IB and PIB for isobutylene and polyisobutylene, respectively, MeCl for methyl chloride (chloromethane), CH$_2$Cl$_2$ for methylene chloride (dichloromethane), TMEDA for tetramethylethylenediamine, HDCCl for hindered dicumyl chloride (chemical name: 1-(tert-butyl)-3,5-bis(2-chloropropan-2-yl)benzene), ATMS for allyl trimethyl silane. MW and MWD signify number average molecular weight ($M_n$) and molecular weight distribution ($M_w/M_n$), respectively. The symbol $f_n$ stands for number average end function.

Materials and Techniques

The source and purity of materials used have been described (see, K. Toth, N. Nugay, J. P. Kennedy, *J. Polym. Sci., Part A: Polym. Chem.* 2016, 54, 532-543), the disclosure of which in incorporated herein by reference in its entirety. Product molecular weights and molecular weight distributions were determined by gel permeation chromatography (GPC), and their structures were characterized by proton nuclear magnetic resonance ($^1$H NMR) spectroscopy. Details of these techniques have been described in, for example, K. Toth, N. Nugay, J. P. Kennedy, *J. Polym. Sci., Part A: Polym. Chem.* 2016, 54, 532-543, the disclosure of which is incorporated herein by reference in its entirety Experimental Conditions and Equipment Experiments were carried out by adding $TiCl_4$ coinitiator to initiate the living cationic polymerization of IB using charges consisting of monomer (IB), initiator (HDCCl), proton trap (TMEDA) and refluxing solvent(s). The reaction apparatus used for the following experiments is shown in FIG. 1 and/or as described below.

EXPERIMENTS

Experiments 1a and 1b

A series of two experiments were carried out to demonstrate ideal temperature control in the living cationic polymerization of isobutylene achieved by the use of refluxing solvents. Thus, one experiment (Experiment 1a) was carried out using conventional external cooling (non-reflux), and another experiment (Experiment 1b) was carried out using refluxing propane. The conventional experiment (1a) was carried out by initiating the polymerization through the addition of $TiCl_4$ (11.68 mmol) to an externally cooled (dry ice bath at −78° C.) mechanically stirred charge of IB (35.33 mmol), a $CH_2Cl_2$/hexane (40/60) solvent mixture, an initiator (HDCCl) (0.73 mmol), and proton trap (TMEDA) (3.65 mmol). The reaction was allowed to stir for 15 min. The addition of the coinitiator elicited an undesirable and immediate sharp temperature jump from about −78° C. to about −61° C. and a similar, albeit lower, jump in temperature upon adding the terminating agent (ATMS) (7.3 mmol). See, FIG. 5A.

Figure 5A:
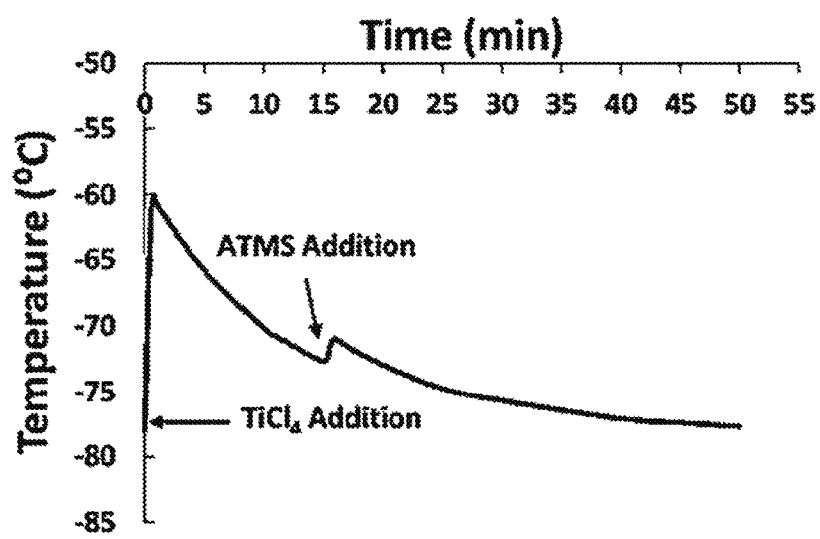
FIGS. 5A-B are graphs showing temperature vs. time profiles of experiments carried out under conventional (non-reflux) cooling (FIG. 5A), and with a refluxing propane solvent (FIG. 5B).
Figure 5B:
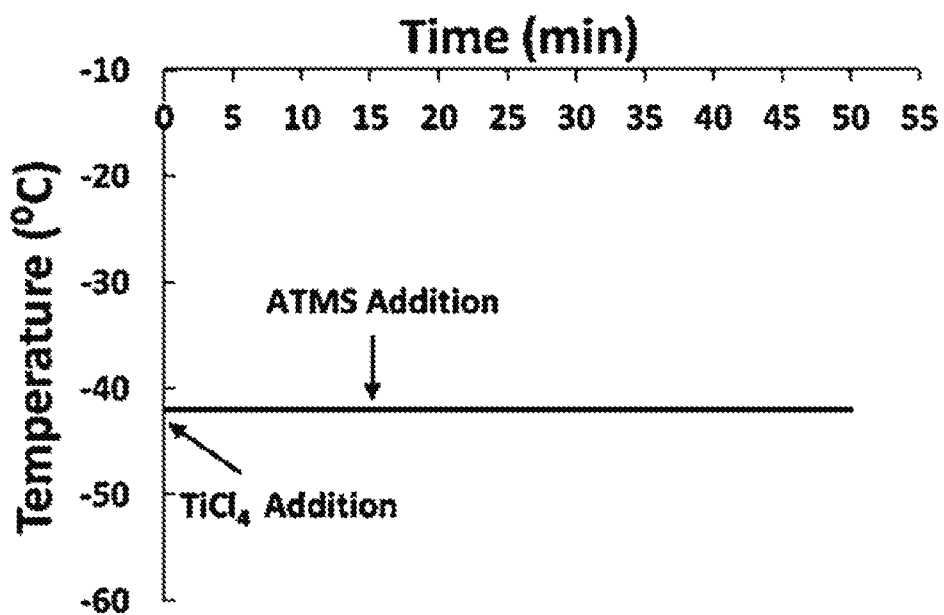

Subsequently, a second polymerization (1b) was carried out under similar conditions (same reagents and reagent concentrations) except using refluxing propane as the solvent, rather than the 60/40 v/v mixture of Hexane and methylene chloride used in Experiment 1a. FIGS. 5A-B contrast the temperature profiles obtained in Experiments 1a and 1b. As can be seen, Experiment 1a (carried out with conventional externally cooled charge) displayed an undesirable and sudden temperature jumps upon the addition of the coinitiator, and 15 minutes later upon the addition of the terminating agent. See, FIG. 5A. In contrast, Experiment 1b (conducted with refluxing propane solvent) proceeded at −42° C. (the boiling point of propane) with no change in temperature upon $TiCl_4$ or ATMS addition. See, FIG. 5B.

Both experiments produced close to 100% monomer conversions. The conventional technique yielded the expected allyl-telechelic PIB with a $M_n$ of ~3100 g/mole and a MWD of 1.07; however, the experiment with refluxing propane (Experiment 1b) yielded a bimodal product; specifically, a main product of $M_n$~3950 g/mol and ~20% of a high molecular weight species ($M_n$~50,000 g/mol). See, FIGS. 3, 4, 7 and 8. Such bimodal distribution is typical for the presence of undesirable side reactions (proton elimination, coupling, see Schemes 1 and 2, above and Scheme 3, below), which compromise living polymerization. It is believed that these side reactions were due to the use of an exclusively nonpolar medium in Experiment 1b and the reduced rate of polymerization at the higher temperature. To test this hypothesis, a series of experiments (Experiments 2a-g) were carried out by the use of refluxlng propane/MeCl solvent mixtures at various propane/MeCl ratios.

Experiments 2a Through 2g

This series of experiments was carried out to investigate the effect of the addition of a polar solvent (MeCl) to the propane used in Experiment 1b on living isobutylene polymerization, as well as the effect of the relative polar solvent (MeCl) concentration on the reaction. Specifically, allyl telechelic PIBs were prepared by living isobutylene polymerization using refluxing propane/MeCl solvents mixtures at various propane/MeCl volume ratios, but otherwise under identical conditions.

These polymerizations yielded close to 100% monomer conversions and the resulting products were characterized in terms of their molecular weights and molecular weight distributions by GPC ($M_n$, $M_w/M_n$), and structure by $^1$H NMR spectroscopy (number of allyl groups per molecule, $f_n$).

The experimental conditions for these experiments (Experiments 2a-2g) were as follows: into a 3 neck 250 mL round bottom flask externally cooled by a removable Dry Ice bath (−55° C.), and equipped with a Teflon-covered stirring bar, a thermocouple and a reflux condenser (cold finger), were condensed 80 mL of a refluxing solvent/solvent mixture composed of propane and methyl chloride mixtures at ratios of 100/0 (Experiment 2a), 90/10 (Experiment 2b), 75/25 (Experiment 2c), 72.5/27.5 (Experiment 2d), 65/35 (Experiment 2e), 60/40 (Experiment 2f), and 0/100 (Experiment 2g) by volume. To the stirred system were added IB monomer (1.98 g, 35.33 mmol), HDCCl initiator (0.21 g, 0.73 mmol), and TMEDA proton trap (0.254 g, 2.19 mmol), in this order. These quantities of reagents were used to produce an allyl telechelic PIB product (allyl-PIB-allyl) having a $M_n$ of ~3000 g/mol. The system was brought to reflux by removing the Dry Ice cooling bath. As will be apparent, the actual reflux temperature will depend on the propane (bp −42.0° C.) and MeCl (bp −24.2° C.) ratio. (See, FIG. 2) To the quiescently refluxing colorless systems was added $TiCl_4$ coinitiator (2.21 g, 11.68 mmol), which immediately changed the color of the system to pale yellow and elicited a higher rate of reflux for 2-4 seconds. The system was allowed to reflux for 15 minutes at which time the ATMS terminating agent (0.83 g, 7.3 mmol) was added. After 45 mins of further refluxing the reaction was MeOH (~12 mL) was added, which discharged the pale yellow color. The reflux condenser was removed and the volatiles were evaporated at room temperature under a hood. All of the products were colorless viscous liquids.

Experiment 2a (100/0 Vol. % Refluxing Propane/Methyl Chloride)

Figure 3:
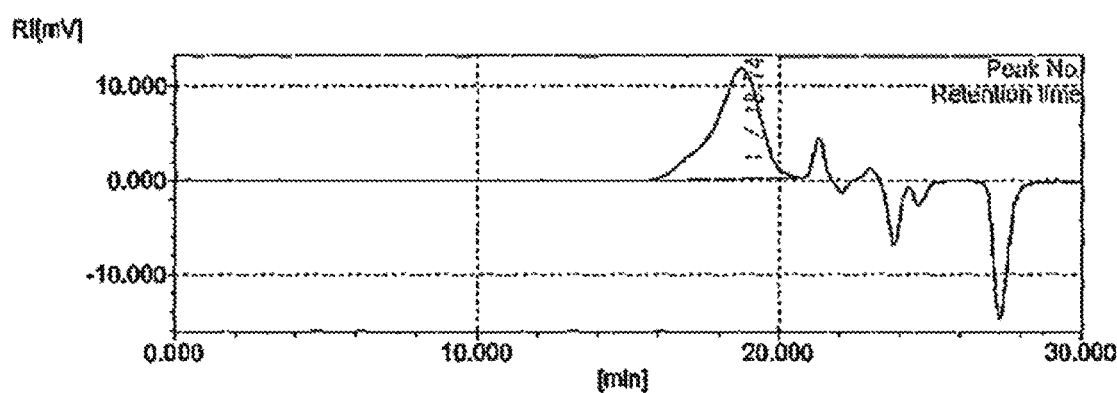
FIG. 3 is a GPC trace of an allyl telechelic PIB obtained using 100% refluxing propane solvent.
Figure 4:
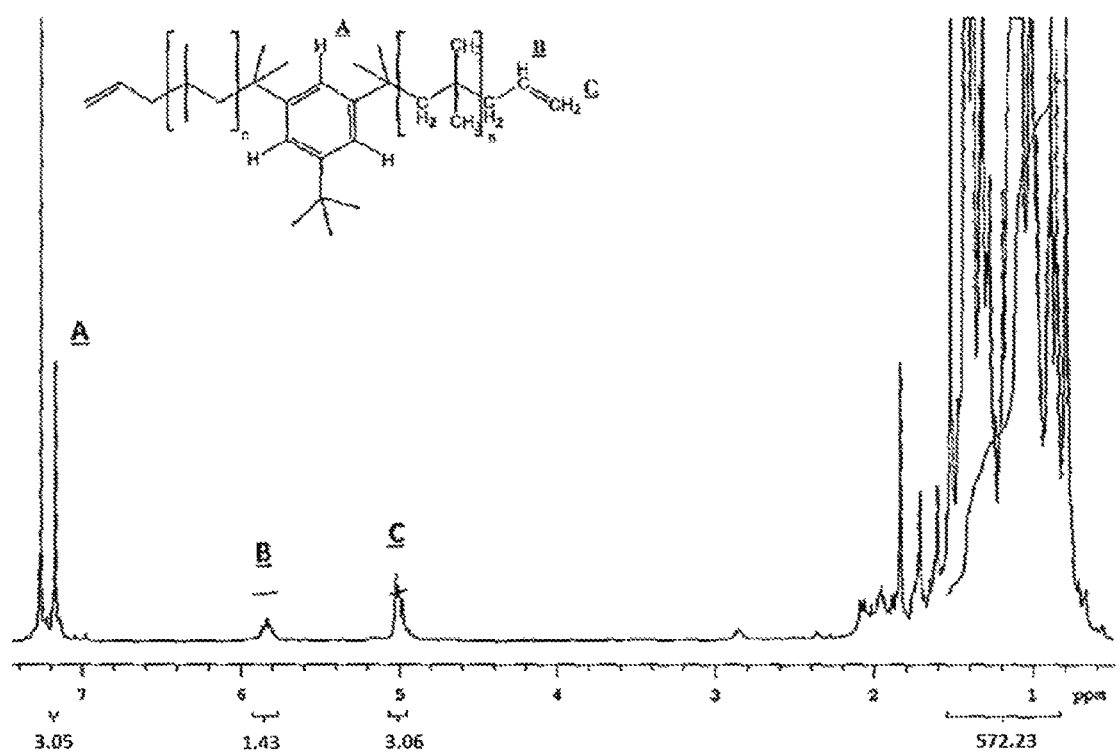
FIG. 4 is a $^1H$ NMR spectrum of an allyl telechelic PIB obtained using refluxing propane solvent.

In this experiment the solvent was 100% propane. FIGS. 3 and 4 show the GPC trace and the $^1$H NMR spectrum of the product, respectively. The GPC trace (FIG. 3) showed the presence of a low molecular weight main product (peak at ~18.5 min, $M_n$~3950 g/mol, and $M_n/M_w$=1.77), and a lesser amount of high molecular weight product (broad shoulder at ~17 min, $M_n$~50,000 g/mol). The $M_n$ of the main product was not far from the theoretical value (3000 g/mol) expected from the reagent concentrations employed.

FIG. 4 shows the $^1$H NMR spectrum together with assignments: $^1$H NMR δ: 7.18 ppm (singlet, 3H, aromatic), 5.82 ppm (multiplet, 2H, vinyl), 5.0 ppm (multiplet, 4H, vinyl), 0-2 ppm (multiplet, aliphatic protons of PIB). According to this evidence, the number average allyl functionality ($f_n$) was 1.50-1.54 (75-77% allyl functionality). Thus, the product was not well-defined allyl-telechelic PIB, as its $M_n$ was significantly higher than theoretical, its MWD was bimodal, and its $f_n$ was noticeably less than the theoretical 2.0.

Experiment 2b (90/10 Vol. % Refluxing Propane/Methyl Chloride)

Figure 9:
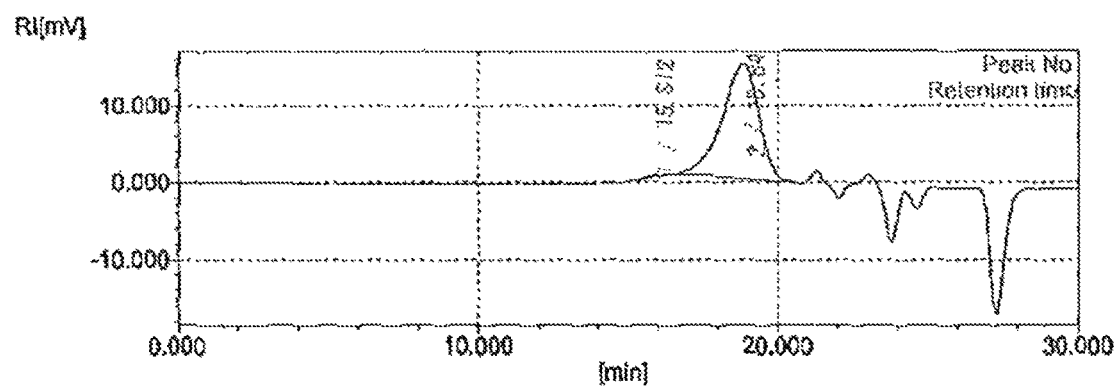
FIG. 9 is a GPC trace of the allyl telechelic PIB according to one or more embodiment of the present invention obtained using a 90/10% refluxing propane/MeCl mixture.

In this experiment the solvent was a mixture of 90/10 vol. % refluxing propane/MeCl. The GPC trace of the product produced in this experiment (see, FIG. 9) showed a mixture of two species, with the main low molecular weight product at 18.5 min ($M_n$=3540 g/mol and $M_w/M_n$~1.38), and a minor high molecular weight component at ~16 min ($M_n$~53,000 g/mol). The $^1$H NMR spectrum of the product (not shown) indicated $f_n$=1.90-1.94 (95-97% allyl functionality).

According to the data, the allyl telechelic PIB product produced in this experiment was contaminated by a high molecular weight species and the $f_n$ was noticeably less than 2.0.

Experiment 2c (75/25 Vol. % Refluxing Propane/Methyl Chloride)

Figures 10, 11:
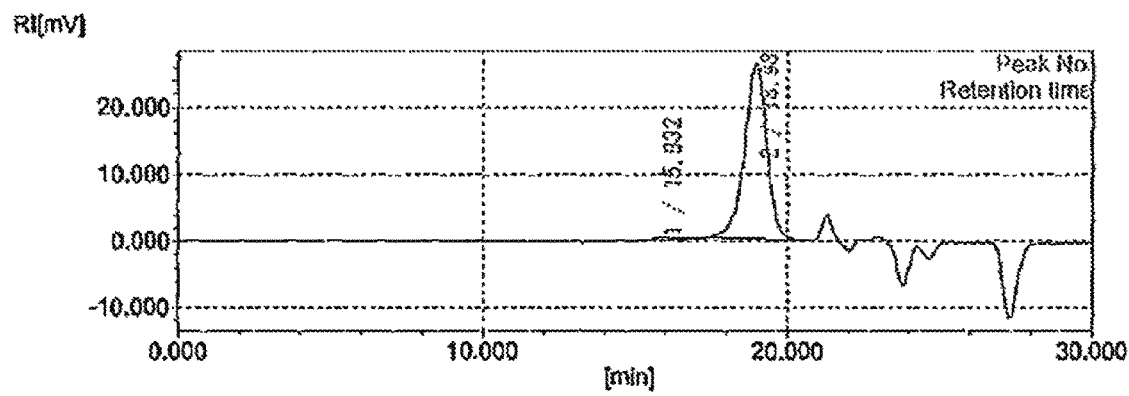
FIG. 10 is a GPC trace of the allyl telechelic PIB according to one or more embodiment of the present invention obtained using a 75/25% refluxing propane/MeCl mixture.
FIG. 11 is a $^1H$ NMR spectrum of allyl telechelic PIB according to one or more embodiment of the present invention obtained using a 75/25% refluxing propane/MeCl mixture

In this experiment, the solvent was a mixture of 75/25 vol. % refluxing propane/MeCl. The GPC trace of the product produced in this experiment (see, FIG. 10) showed a mixture of two species, with the main low molecular weight product at 18.5 min ($M_n$=3100 g/mol, and $M_w/M_n$~1.14), and a very minor high molecular weight component at ~16 min ($M_n$~44,000 g/mol). The $^1$H NMR spectrum (see, FIG. 11) showed virtually quantitative allyl functionalization ($f_n$=2.0). Even though the GPC indicated a very small (trace) amount of a high molecular weight byproduct, it is evident that increasing the MeCl concentration from 0 to 25% enhances the quality of the product (within the accuracy of 500 MHz $^1$H NMR spectroscopy the product is allyl telechelic PIB).

Experiment 2d (72.5/27.5 Vol. % Refluxing Propane/Methyl Chloride)

This experiment was essentially a repeat of Example 2c, with the propane/MeCl ratio=72.5/27.5. According to GPC (not shown), the main product formed in this experiment had a $M_n$ of 3100 g/mol and $M_w/M_n$ of 1.14, and there was still a trace of the high molecular weight byproduct. The $^1$H NMR spectrum (not shown) showed virtually quantitative allyl functionalization, $f_n$=2.0.

Experiment 2e (65/35 Vol. % Refluxing Propane/Methyl Chloride)

Figure 12:
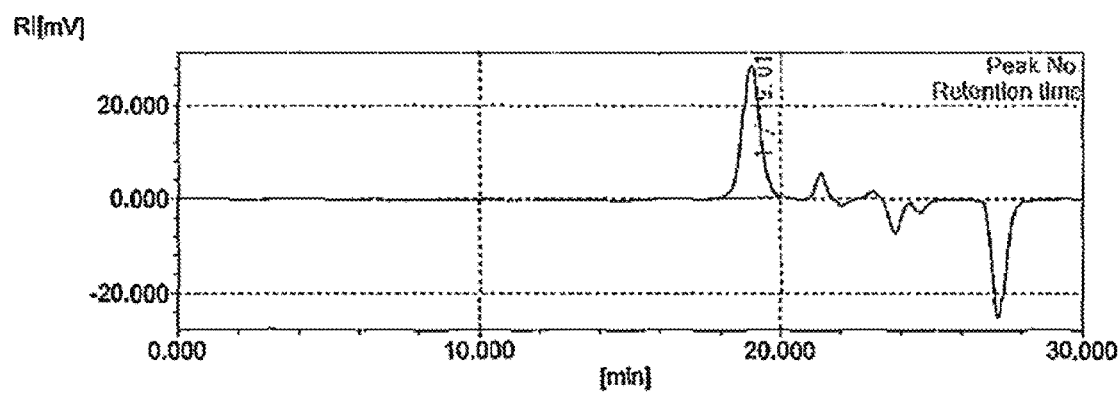
FIG. 12 is a GPC trace of allyl telechelic PIB according to one or more embodiment of the present invention obtained using a 65/35% refluxing propane/MeCl mixture.

In this experiment the solvent was a mixture of 65/35 vol. % refluxing propane/MeCl. The GPC trace of the product formed in this experiment (FIG. 12) showed the presence of only one species with a $M_n$ of 2960 g/mol and $M_w/M_n$ of 1.09. The NMR spectrum (not shown) showed virtually quantitative allyl functionalization, $f_n$=2.0. According to this evidence, allyl telechelic PIB obtained in a 65/35 refluxing propane/MeCl mixture exhibits close to theoretical $M_n$, monomodal $M_w/M_n$, and $f_n$.

Experiment 2f (60/40 Vol. % Refluxing Propane/Methyl Chloride)

In this experiment the solvent was a mixture of 60/40 vol. % refluxing propane/MeCl. GPC of the product produced by this experiment (not shown) indicated the presence of only one species having a $M_n$ of 3310 g/mol and a $M_w/M_n$ of 1.07, and NMR spectroscopy (not shown) showed allyl telechelic PIB with virtually quantitative allyl functionalization ($f_n$=2.0). According to this evidence, allyl telechelic PIB obtained in a 60/40 vol % refluxing propane/MeCl mixture exhibits close to theoretical $M_n$, as well as monomodal $M_w/M_n$, and $f_n$.

Experiment 2g (0/100 Vol. % Refluxing Propane/Methyl Chloride)

Figure 13:
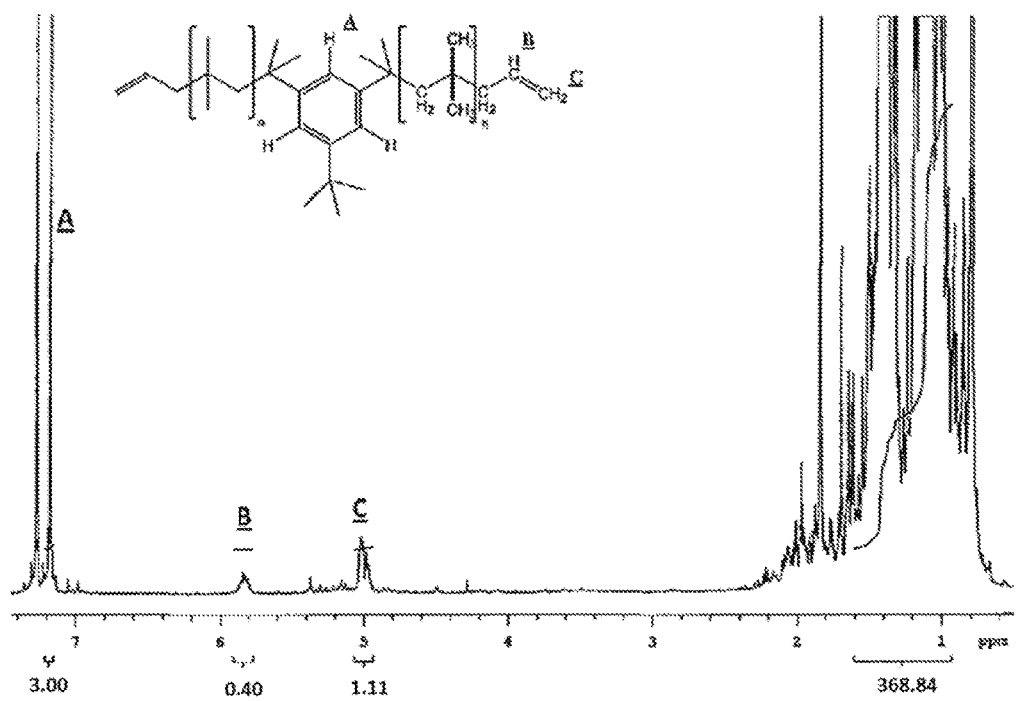
FIG. 13 is a $^1H$ NMR spectrum of a representative allyl telechelic PIB obtained in refluxing MeCl solvent.

Four duplicate experiments were carried out with refluxing MeCl solvent (no propane). The averages are reported: GPC (not shown) showed a main product with a $M_n$ of 3140 g/mol and $M_w/M_n$ of 1.2, and the presence of a small amount (~5%) of a high molecular weight species having a $M_n$ of ~45,000 g/mol. $^1$H NMR spectroscopy (see, FIG. 13) showed 20-30% allyl functionalization, i.e., $f_n$=0.4-0.6, and the presence of various double bonds indicating proton elimination (see the various small resonances in the 4.5 to 5.5 ppm region).

Figure 14:
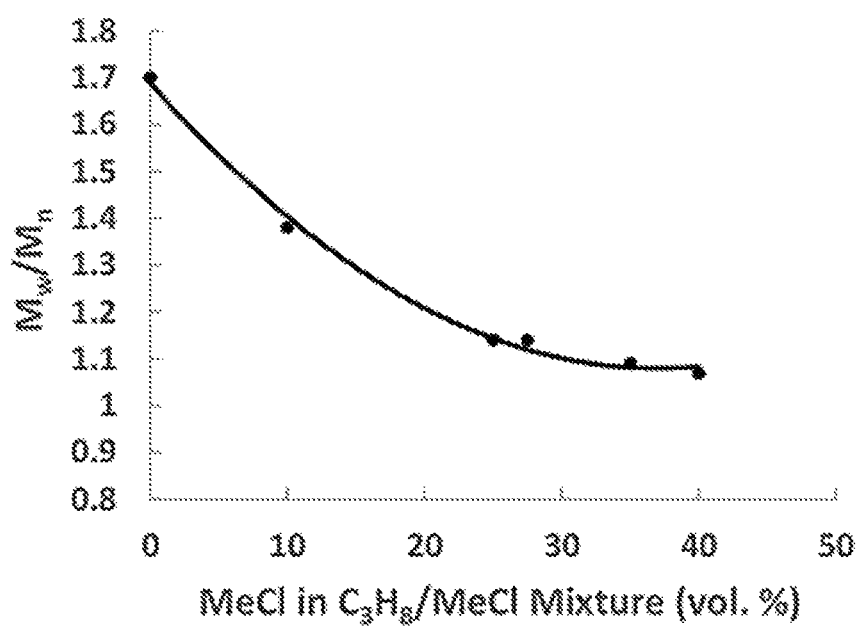
FIG. 14 is a graph showing the effect of $C_3H_8$/MeCl composition on the MWD ($M_w/M_n$) of allyl-PIB-allyls prepared according to one or more embodiment of the present invention.

It was found that well-defined allyl telechelic PIB was obtained only by the use of mixed refluxing propane/MeCl solvent systems, and that use of propane or MeCl exclusively yields mixtures of products. The beneficial effect of the polar solvent is likely due to solvating and thus stabilizing active cations by MeCl dipoles. Solvated ions are less likely to undergo proton elimination (chain transfer, see above) than unsolvated ion pairs. FIG. 14 shows $M_w/M_n$ (i.e., molecular weight distribution) as a function of MeCl concentration in propane/MeCl solvent mixtures. The relatively broad distribution obtained in propane becomes narrower with increasing MeCl concentration and reaches $M_w/M_n$<1.1 at ~35 vol % MeCl, which suggests living polymerization.

Experiments 3a-3c

This series of polymerizations was carried out using refluxing 65/35 propane/MeCl solvent mixtures under the conditions specified above except the individual polymerizations were terminated by the addition of ATMS at 3 (Experiment 3a), 5 (Experiment 3b), and 10 (Experiment 3c) minutes after TiCl$_4$ addition. FIG. 6B shows molecular weights ($M_n$) as a function of conversion (%), together with $M_w/M_n$ values obtained at 3, 5, and 10 mins. The line is the theoretical line for a living polymerization. The linearity of the plot indicates living polymerization. This conclusion is further substantiated by the insert which shows the number of molecules formed (N) per the number of initiator molecules employed ($I_o$). Evidently, the number of molecules remains constant during the polymerization, i.e., the system is living.

Experiments 3d

This polymerization was carried out using refluxing 65/35 propane/MeCl solvent mixtures under the conditions specified above except the polymerization was terminated by the addition of ATMS at 15 minutes after $TiCl_4$ addition. This polymerization showed close to 100% conversion and $M_n$=2960 g/mol with $M_w/M_n$~1.09 (i.e.; absence of by products) which also indicates livingness. According to this data, well-defined allyl telechelic PIB can be obtained by terminating polymerization at least 15 minutes after coinitiator addition (i.e., in the absence of monomer). After 15 minutes side reactions may occur and compromise product quality.

Example 2

Abbreviations

In this Example, the following abbreviations are used: IB and PIB for isobutylene and polyisobutylene, respectively, $C_3H_8$ for propane, MeCl for methyl chloride (chloromethane), TMEDA for tetramethylethylene-diamine, ED for electron donor, HDCCl for hindered dicumyl chloride (chemical name: 1-(tert-butyl)-3,5-bis(2-chloropropan-2-yl)benzene), ATMS for allyltrimethylsilane. MW and MWD signify number average molecular weight and molecular weight distribution, respectively. $f_n$ stands for number average end function.

Materials and Techniques

Propane (99.5% purity) and methyl chloride (99.9% purity) were purchased from Praxair and were used without purification. Product MWs and MWDs were determined by gel permeation chromatography using a Tosoh EcoSec HLC-8320GPC THF instrument and flow rate of 1.0 mL/min. The instrument was equipped with two TSKgel® columns, one TSKgel® guard column and a Bryce-type differential refractometer (RI) detector. Spectra were analyzed by EcoSEC®GPC work station software. Structures were characterized by $^1$H NMR spectroscopy. Details of these techniques have been described in K. Toth, N. Nugay, J. P. Kennedy, *J. Polym. Sci., Part A: Polym. Chem.* 2016, 54, 532-543, the disclosure of which is incorporated herein by reference.

Syntheses were carried out by adding $TiCl_4$ coinitiator to charges consisting of monomer (IB), initiator (HDCCl), electron donor (TMEDA) and refluxing solvent(s); and allyl functionalization was effected by the addition of the terminating agent allyltrimethylsilane (ATMS). FIG. 1 shows the equipment used.

RESULTS AND DISCUSSION

1. Demonstrating Ideal Temperature Control

A comparative experiment was carried out to demonstrate temperature control by the use of a refluxing charge. Thus, one experiment was carried out with conventional external cooling (non-reflux) routinely used for the synthesis of allyl-PIB-allyl, and another with refluxing propane.

The conventional experiment was carried out by adding $TiCl_4$ (11.68 mmol) to a removable externally cooled (Dry Ice/isopropanol bath, −78° C.) mechanically stirred charge of IB (35.33 mmol), $CH_2Cl_2$/hexane (80 mL, 40/60 v/v) solvent mixture, initiator (HDCCl, 0.73 mmol) and electron donor (TMEDA, 3.65 mmol). After stirring the charge for 15 min the polymerization was terminated by addition of ATMS (7.3 mmol). $TiCl_4$ addition elicited an immediate sharp temperature jump to −61° C. and a similar albeit lesser jump upon adding ATMS.

The reflux experiment was carried out under similar conditions (same reagents and reagent concentrations) except using refluxing propane solvent. FIGS. 5A-B contrast the temperature profiles obtained: The experiment with conventional externally cooled charge displayed undesirable sudden temperature jumps upon adding the coinitiator, and 15 minutes later the terminating agent. In contrast, the experiment with refluxing propane proceeded at a constant −42.5° C. (the boiling point of propane) with no change in temperature upon $TiCl_4$ and ATMS addition.

Both experiments produced allyl-PIB-allyl with near quantitative monomer conversions. According to GPC analysis the conventional technique yielded the expected MW ($M_n$~3100 g/mole) and narrow MWD ($M_w/M_n$=1.07); however, the experiment with refluxing propane yielded bimodal product, i.e., a main product ($M_n$=~3950 g/mol) and ~20% of high molecular weight contaminant ($M_n$=~50,000 g/mol), indicating the presence of undesirable side reactions (proton elimination, coupling; see above) during synthesis.

Evidently, ideal temperature control can be achieved by the use of refluxing propane at −42.5° C.; however, the product is a mixture of species, due to side reactions. It is hypothesized that the side reactions in refluxing propane were due to (a) reduced rate of polymerization in nonpolar propane (dielectric constant ~1.6), and/or (b) delayed (15 mins) termination time. The relatively higher temperature of −42.5° C. was not considered detrimental for living IB polymerization as livingness has been demonstrated even at −10° C. To test this hypothesis experiments were carried out (a) using various refluxing $C_3H_8$/MeCl mixtures, and (b) terminating polymerizations at shorter (and longer) than 15 mins.

2. Effect of Refluxing $C_3H_8$/MeCl Mixtures on MW, MWD, and Structure

The objective of this series of experiments was to investigate the effect of polar MeCl solvent (dielectric constant ~12.6) and its concentration on living isobutylene polymerization and subsequent allylation. The large effect of even small changes in polarity on living IB polymerizations has amply been documented. Thus, allyl-PIB-allyls were prepared at various volume ratios of refluxing C3C8/MeCl mixtures, and the MW, MWD and structures of the products were determined.

Synthesis and termination (allylation) conditions were as follows: Into a 3 neck 250 mL round bottom flask equipped with a Teflon-covered stirring bar, thermocouple and reflux condenser and externally cooled by a Dry Ice bath, were condensed 80 mL of propane/methyl chloride mixture at v/v 100/0, 90/10, 75/25, 72.5/27.5, 65/35, 60/40, and 0/100. To the stirred systems were added IB monomer (1.98 g, 35.33 mmol), HDCCl initiator (0.21 g, 0.73 mmol), and TMEDA electron donor (0.254 g, 2.19 mmol) to produce $M_n$=3000 g/mol PIB. The systems were brought to reflux by removing the Dry Ice cooling bath. Optionally, the rate of reflux was controlled by immersing the reactor in ice water.

Figure 2:
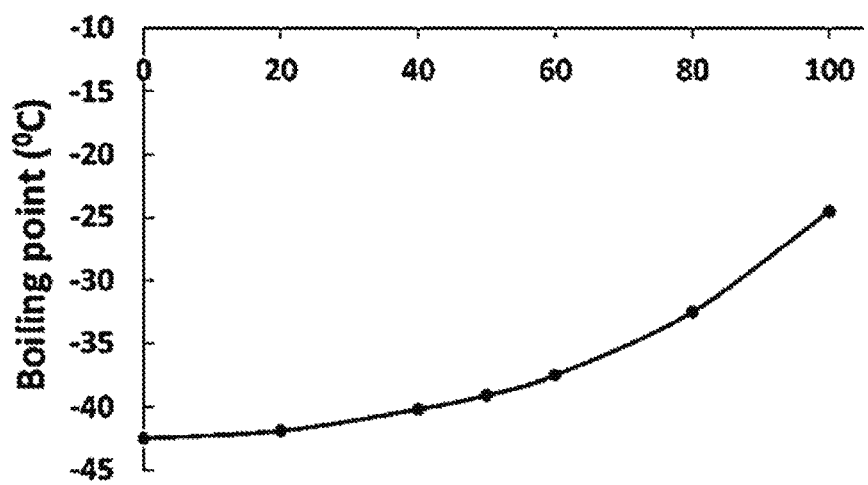
FIG. 2 is a graph showing reflux temperatures of $C_3H_8$/MeCl (v/v) mixtures.

The boiling points of $C_3H_8$ and MeCl (−42.5 and −24.2° C., respectively), and the reflux temperatures of their mixtures were determined (FIG. 2). Unexpectedly, the boiling point versus $C_3H_8$/MeCl composition plot showed a strong negative deviation from ideality suggesting repulsion between the components. The reflux temperature of 60/40 $C_3H_8$/MeCl mixture (which is of particular interest to us, see below) was −40.2° C.

To the quiescently refluxing colorless charges was added $TiCl_4$ coinitiator (2.21 g, 11.68 mmol), which immediately changed the color of the refluxing system to pale yellow and elicited a higher rate of reflux for a few (2-4) seconds. Polymerizations were allowed to proceed for 15 minutes and were terminated with ATMS (0.83 g, 7.3 mmol). After 45 mins of further reflux the reaction was quenched with MeOH (~12 mL), which gradually discharged the pale yellow color. The reflux condenser was removed, the volatiles were evaporated at room temperature in a hood, and the products were washed with aqueous NaHCO3 and precipitated in methanol. All the products were colorless viscous liquids. All polymerizations yielded near quantitative conversions. Products were characterized by GPC ($M_n$, $M_w/M_n$), and by $^1$H NMR spectroscopy (number of allyl groups per molecule, $f_n$).

According to GPC (FIG. 7) the allyl-PIB-ally formed in 100% propane is a mixture. In the presence of increasing amounts of MeCl the contaminating high MW component gradually diminished (see decreasing hump/shoulder between 15-17 min elution counts) and finally disappeared with 60/40 v/v $C_3H_8$/MeCl. Further, as shown by the data in FIG. 14, the MWD of allyl-PIB-allyl narrowed with increasing MeCl content and at ~65/35 v/v $C_3H_8$/MeCl was close to the theoretical limit ($M_w/M_n$=1.0) characteristic of living polymerizations.

The beneficial effect of the polar solvent is likely due to solvation stabilizing the growing cation. It is known that solvated ion pairs are less likely to undergo proton loss than unsolvated ion pairs. (See, e.g., G. Erdodi, J. Kang, J. P Kennedy, E. Yilgor, I. Yilgor, J. Polym. Sci.: Part A: Polym. Chem., 2009, 47, 5278-5290 at p. 6 and U.S. Published Patent Application No. 1988/4758631 to J. P. Kennedy et al. at p. 21, the disclosure of which are incorporated herein by reference.) Surprisingly, however, four duplicate experiments showed that allyl-PIB-allyl formed in refluxing 100% MeCl was a mixture of the expected main product ($M_n$=3140 g/mol), plus very small amount of high MW (Mn~45,000) species.

Figure 8:
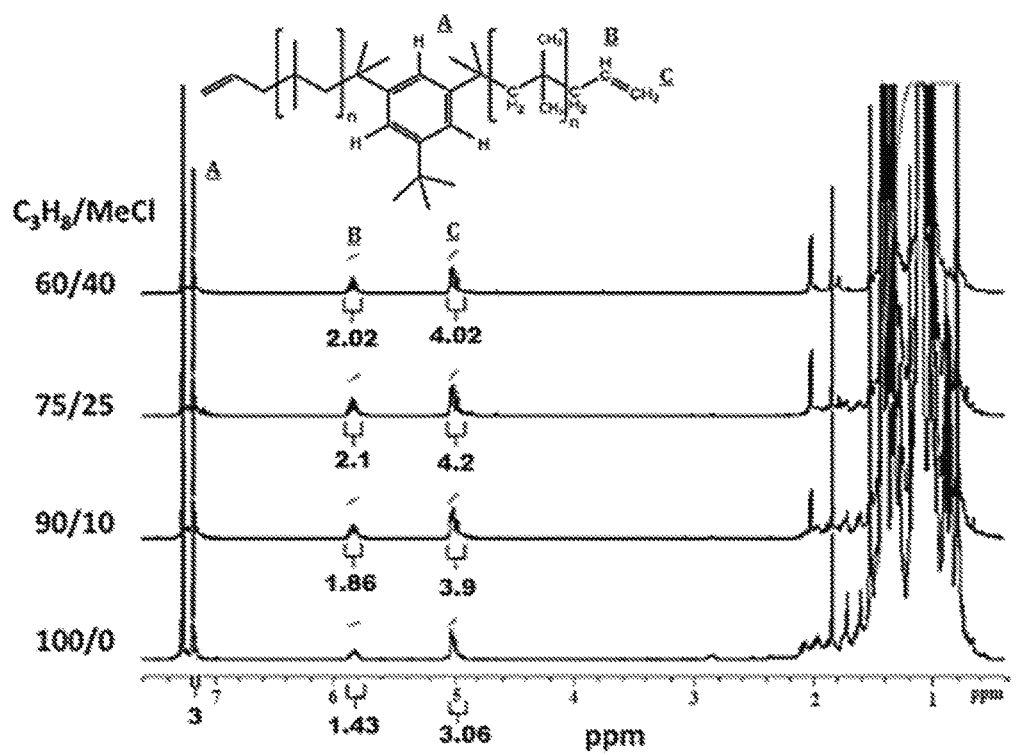
FIG. 8 is a $^1H$ NMR spectra of allyl-PIB-allyls obtained at various $C_3H_8$/MeCl v/v ratios. $^1H$ NMR (500 MHz, CDCl3, δ): 7.18 ppm (singlet, 3H, aromatic), 5.82 ppm (multiplet, 2H, vinyl), 5.0 ppm (multiplet, 4H, vinyl), 0-2 ppm (multiplet, aliphatic protons of PIB).

Product structures were characterized by $^1$H NMR spectroscopy. FIG. 8 shows representative spectra of allyl-PIB-allyls obtained using various $C_3H$/MeCl compositions together with key assignments. Allylation was quantitative $f_n$=2.0) using 60/40 and 75/25 $C_3H$/MeCl, but less than quantitative ($f_n$=1.86) using 90/10 $C_3H_8$/MeCl, and much less than quantitative (75-77%, $f_n$=1.50-1.54) using 100/0 $C_3H$/MeCl. Much less allylation (20-30%, $f_n$=0.40.6) was observed using 0/100 $C_3H$/MeCl (NMR spectrum not shown).

According to this data, well-defined ($f_n$=2.0) allyl-PIB-allyl with close to theoretical MW ($M_n$=3000 g/mol) and narrow MWD ($M_w/M_n$=1.07) was prepared in refluxing 60/40 v/v $C_3H$/MeCl at ~−40° C.

3. The Effect of Termination Time

Despite the great interest of living IB polymerizations, there does not appear to be any published information as to the effect of reaction time (i.e., the time of termination) on the MW, MWD and structure of PIB produced in general, and of allyl-PIB-allyl in particular. As mentioned above, we hypothesized that undesirable side reactions may occur if the polymerization is carried out at a relatively higher temperature (i.e., at ~−40° C. or higher) and the reaction is not terminated immediately upon 100% monomer conversion, i.e., if active cations remain after monomer depletion. Thus we studied the effect of termination time at −40° C., by determining the MW, MWD and structure of allyl-PIB-allyl obtained in refluxing 60/40 v/v $C_3H_8$/MeCl. Polymerizations were terminated 3, 5, 10, 15, 60, 120 and 180 mins after TiCl$_4$ addition. Experimental conditions were those described above, i.e., 80 mL solvents, IB=35.53 mmol, HDCCl=0.73 mmol, TMEDA=2.19 mmol, TiCl$_4$=11.68 mmol; termination with ATMS=7.3 mmol; the 60 and 120 mins samples were obtained by withdrawing ~4 mL aliquots from the refluxing system.

Figure 6A:
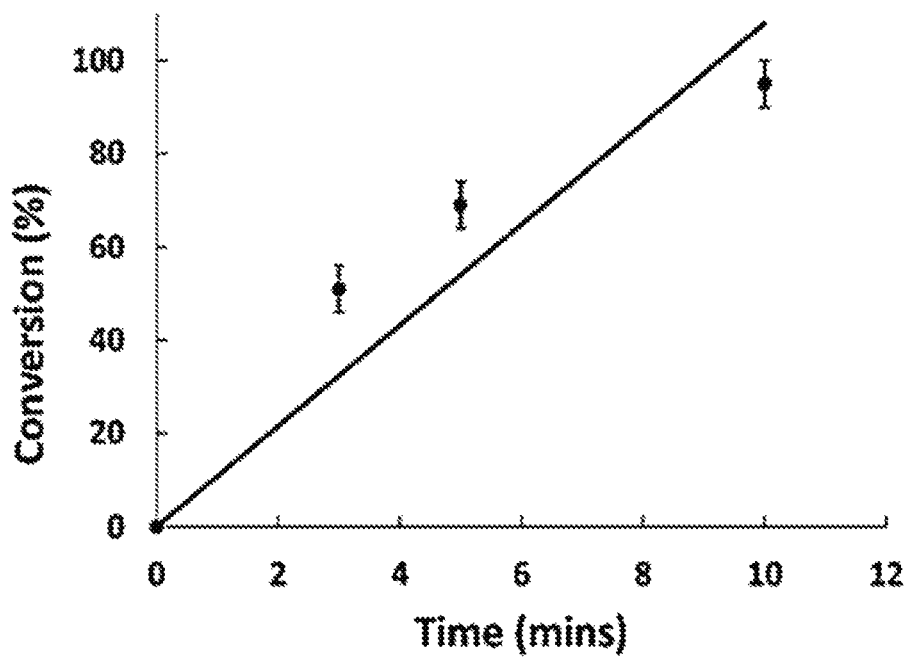
FIGS. 6A-B are graphs showing: conversion of monomer versus time (FIG. 6A); and molecular weight (Mn) versus conversion (%) (Insert: Number of polymer molecules (N/I$_o$) formed versus time) (FIG. 6B).
Figure 6B:
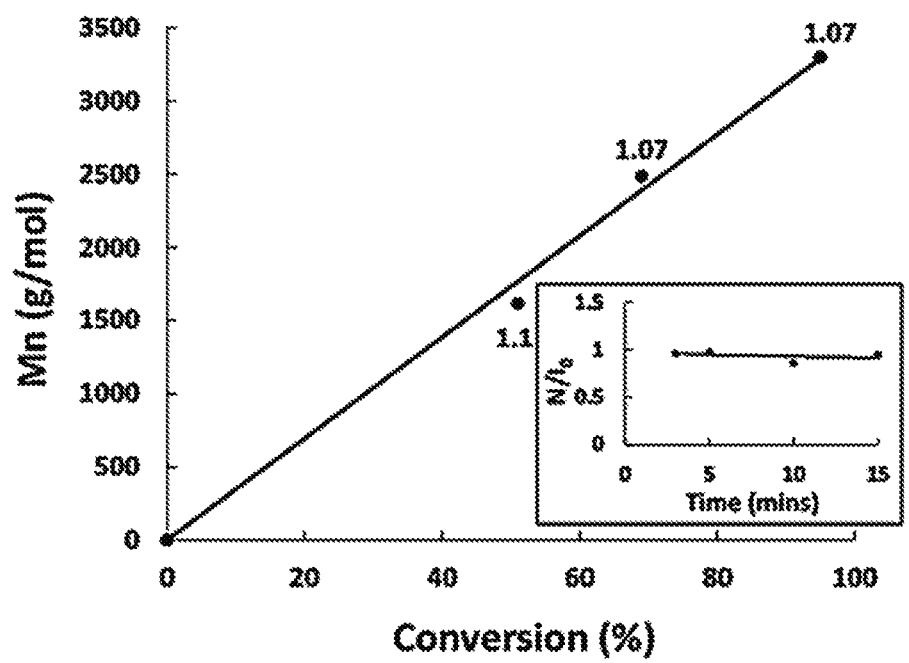
Figure 7:
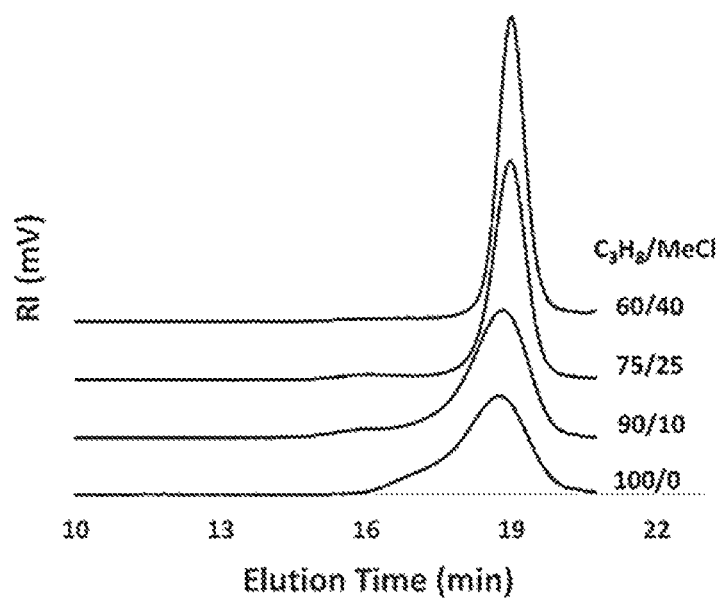
FIG. 7 is a graph showing GPC traces of allyl-PIB-allyls obtained in various refluxing $C_3H_8$/MeCl charges (solvent compositions shown).

FIG. 6A shows conversion versus time, and FIG. 6B shows $M_n$ versus % conversion together with $M_w/M_n$ obtained in the 0-10 mins range. As shown in FIG. 6A conversions reached near quantitative values in ~10 mins, and as shown in FIG. 6B the experimental values fell on the solid theoretical line indicating living polymerizations. The latter conclusion was substantiated by plotting the number of polymer molecules formed (N/I$_o$, where N=number of molecules formed and I$_o$=moles of initiator) as a function of time (see insert in FIG. 6B). The horizontal plot indicates that the number of molecules remained constant during polymerization, i.e., the system was living during this period.

Further, the 15 mins sample also produced well defined allyl-PIB-allyl($M_n$=2960 g/mol, $M_w/M_n$=1.09, $f_n$=2.0) indicating a dormant but living system. However, samples withdrawn at 60, 120 and 180 minutes showed the presence of byproducts, suggesting side reactions. Specifically, GPC showed a sharp main peak at ~19 min ($M_n$=2900 g/mol) with a distinct shoulder at ~17 min typical of high MW species (the traces were virtually identical to those in FIG. 7). $^1$H NMR spectroscopy showed chemical shifts similar to those in FIG. 8, however, allyl functionalization was much lower than quantitative (~50%, $f_n$~1) According to these observations well-defined allyl-PIB-allyl was obtained at ~−40° C. by terminating the polymerizations 15 mins after coinitiator addition, i.e., livingness persists for at least 5 mins after monomer depletion. At 60 minutes after coinitiator addition and beyond, however, byproducts arise most likely by proton elimination followed by intramolecular alkylation (see above).

CONCLUSIONS

Allyl-PIB-allyl was quantitatively prepared by living IB polymerization followed by termination with ATMS under ideal temperature control at ~−40° C. in refluxing 60/40 v/v $C_3H$/MeCl. However, polymerizations carried out under the same conditions but in refluxing 100% propane or methyl chloride were contaminated by byproducts. The composition of the nonpolar/polar medium must be carefully controlled to obtain living polymerizations. Under well-defined conditions IB conversions increased linearly with time and monomer conversion was complete in ~10 minutes. Contaminating byproducts did not form for at least 5 minutes after monomer depletion; however, they appeared in samples obtained after 60 or more minutes indicating side reactions, i.e., dehydrochlorination, "coupling".

The mechanism proposed to account for these observations is presented in Scheme 3, below.

Scheme 3

The mechanisim of termination and byproduct synthesis in allyl-PIB-allyl synthesis

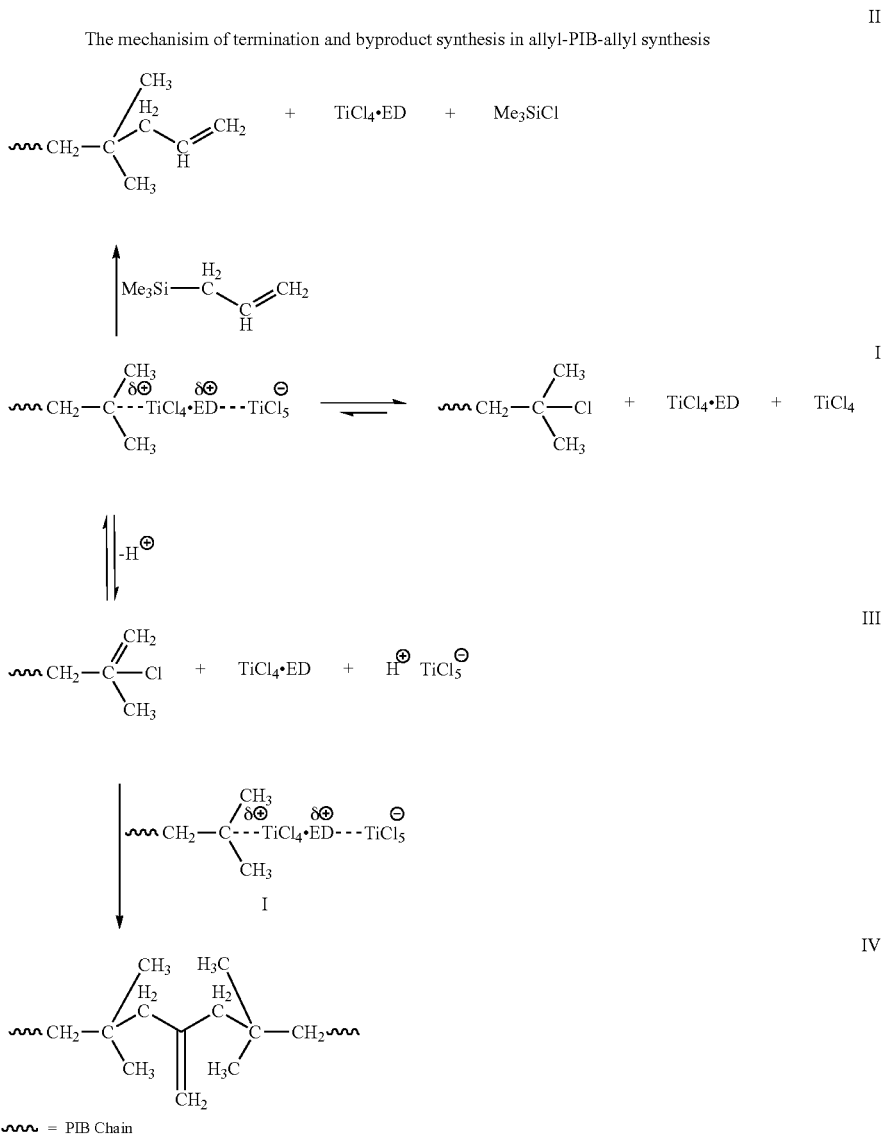

ⵯⵯⵯ = PIB Chain

ED = TMEDA

The starting formula (I) indicates the living carbocation with the charge spread over the TiCl$_4$.ED. The mechanism and the symbolism of living (in fact quasiliving) IB polymerization have been discussed in great detail elsewhere. See, e.g., J. P. Kennedy, B. Ivan, In Designed Polymers by Carbocationic Macromolecular Engineering; Hanser Verlag, Munich, 1992 at p. 60, incorporated herein by reference. The upward vertical arrow indicates the formation of allyl-PIB-allyl (II) by permanent termination (allylation) with ATMS, whose mechanism has also been presented earlier. B. Ivan, J. P. Kennedy, *J. Polym. Sci., Part A: Polym Chem.* 1989, 28, 89-104, the disclosure of which is incorporated herein by reference in its entirety. The living carbocation may lose a proton and reversibly form (mainly) exo terminal unsaturation (III), and finally, the exo unsaturated terminus (III) may also react with the living carbocation (I) and yield coupled high MW byproduct (IV).

In light of the foregoing, it should be appreciated that the present invention significantly advances the art by providing a method for the quantitative preparation of allyl-telechelic polyisobutylene under ideal internal temperature control that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A method for making polyisobutylene by living cationic polymerization of isobutylene comprising:
   A) providing an externally cooled reaction vessel;
   B) charging said externally cooled reaction vessel with isobutylene, an initiator, a refluxing solvent mixture, and a proton trap or electron donor at a temperature below a boiling point for said refluxing solvent mixture;
C) allowing the temperature of the externally cooled reaction vessel to increase to the boiling point of said refluxing solvent mixture causing the refluxing solvent mixture to reflux;
D) inducing living cationic polymerization of the isobutylene by the addition of a co-initiator to said externally cooled reaction vessel to produce polyisobutylene polymer chains; and
E) terminating the living cationic polymerization reaction to produce the polyisobutylene polymer.

2. The method of claim 1 wherein said refluxing solvent mixture comprises a polar solvent and a nonpolar solvent.

3. The method of claim 2 wherein said nonpolar solvent is propane.

4. The method of claim 2 wherein said nonpolar polar solvent is methyl chloride ($CH_3Cl$) or dichloromethane ($CH_2Cl_2$).

5. The method of claim 1 wherein said refluxing solvent mixture has a boiling point of about −40° C.

6. The method of claim 4 wherein volume ratio of propane to methyl chloride in said refluxing solvent mixture is from about 9:1 to about 1:9.

7. The method of claim 4 wherein the ratio of propane to methyl chloride in said refluxing solvent mixture by volume is from about 3:2 to about 7:3.

8. The method of claim 1 wherein the living cationic polymerization reaction is allowed to continue for about 15 minutes or until substantially all of the isobutylene has been reacted before the step of termination (step E).

9. The method of claim 1 wherein the step of terminating the polymerization reaction (step E) comprises adding a termination agent, wherein said termination agent terminates the living cationic polymerization reaction by reacting with said polyisobutylene chains to leave terminal allyl functional groups on said polyisobutylene chains.

10. The method of claim 9 wherein the polyisobutylene polymer produced in step E has a molecular weight distribution of from 1.0 to 1.2 and a number average end functionalization ($f_n$) of from about 1.8 to about 2.0.

11. A method for controlling the temperature for conducting living cationic polymerization of isobutylene above −78° C. comprising:
A) providing an externally cooled reaction vessel;
B) charging said externally cooled reaction vessel with isobutylene, an initiator, a refluxing solvent mixture, and a proton trap at a temperature below a boiling point for said refluxing solvent mixture, wherein said refluxing solvent mixture comprises a polar solvent and a nonpolar solvent;
C) allowing the temperature of the externally cooled reaction vessel to increase to the boiling point of said refluxing solvent mixture causing the refluxing solvent mixture to reflux;
D) inducing living cationic polymerization of the isobutylene by the addition of a co-initiator to said externally cooled reaction vessel to produce polyisobutylene polymer chains; wherein the temperature inside said externally cooled reaction vessel is maintained at or about said boiling point during said living cationic polymerization.

12. The method of claim 11 wherein said nonpolar solvent is propane and said polar solvent is methyl chloride.

13. The method of claim 12 wherein said refluxing solvent mixture comprises from about 60% to about 70% propane and from about 30% to about 40% methyl chloride by volume.

14. A method of making a di-telechelic allyl-functionalized polyisobutylene by living cationic polymerization of isobutylene comprising:
A) providing an externally cooled reaction vessel equipped with a reflux condenser;
B) charging said externally cooled reaction vessel with isobutylene, a bi-functional initiator, a refluxing solvent mixture comprising propane and methyl chloride, and a proton trap at a temperature below a boiling point for said refluxing solvent mixture;
C) allowing the temperature of the externally cooled reaction vessel to increase to the boiling point of said refluxing solvent mixture causing the refluxing solvent mixture to reflux;
D) inducing living cationic polymerization of the isobutylene by the addition of a co-initiator to said externally cooled reaction vessel to produce polyisobutylene polymer chains;
E) allowing living cationic polymerization to continue until substantially all of the isobutylene has been reacted;
F) terminating the living cationic polymerization reaction by adding a termination agent, wherein said termination agent terminates the living cationic polymerization reaction by reacting with said polyisobutylene chains to leave terminal allyl functional groups on said polyisobutylene chains to produce the di-telechelic allyl-functionalized polyisobutylene.

15. The method of claim 14 wherein said refluxing solvent mixture has a boiling point of about −40° C.

16. The method of claim 14 wherein said bi-functional initiator comprises 1-(tert-butyl)-3,5-bis(2-chloropropan-2-yl)benzene (HDCCl).

17. The method of claim 14 wherein the step of terminating (step F) is performed about 15 minutes after the step inducing (step C).

18. The method of claim 14 wherein the step of terminating (step F) is performed not more than 5 minutes after all of the isobutylene has reacted.

19. The method of claim 14 wherein said refluxing solvent mixture comprises from about 60% to about 70% propane and from about 30% to about 40% methyl chloride by volume.

20. The method of claim 14 wherein the di-telechelic allyl-functionalized polyisobutylene produced in step F has a molecular weight distribution of from about 1.0 to about 1.2 and a number average end functionalization ($f_n$) of from about 1.8 to about 2.0.

* * * * *